United States Patent [19]
Wenger

[11] Patent Number: 5,599,771
[45] Date of Patent: Feb. 4, 1997

[54] 3-ARYLURACIL DERIVATIVES AND THEIR USE AS HERBICIDES

[75] Inventor: Jean Wenger, Wallbach, Switzerland

[73] Assignee: Ciba-Geigy Corporation, Tarrytown, N.Y.

[21] Appl. No.: 347,392

[22] PCT Filed: Apr. 11, 1994

[86] PCT No.: PCT/EP94/01109

§ 371 Date: Dec. 16, 1994

§ 102(e) Date: Dec. 16, 1994

[87] PCT Pub. No.: WO94/24128

PCT Pub. Date: Oct. 27, 1994

[30] Foreign Application Priority Data

Apr. 21, 1993 [CH] Switzerland .............. 1207/93

[51] Int. Cl.⁶ .............. C07D 239/54; C07D 239/52; A01N 43/54
[52] U.S. Cl. .............. 504/243; 544/230; 544/311; 544/312; 544/310; 544/313; 544/314; 544/295; 544/296
[58] Field of Search .............. 544/230, 311, 544/312, 310, 313, 314, 295, 296; 504/243

[56] References Cited

U.S. PATENT DOCUMENTS

| | | | |
|---|---|---|---|
| 4,746,352 | 5/1988 | Wenger et al. | 544/312 |
| 4,760,163 | 7/1988 | Wenger et al. | 544/312 |
| 5,183,492 | 2/1993 | Suchy et al. | 504/243 |
| 5,266,554 | 11/1993 | Suchy et al. | 504/243 |
| 5,336,663 | 8/1994 | Wenger et al. | 504/243 |

FOREIGN PATENT DOCUMENTS

| | | |
|---|---|---|
| 0195346 | 9/1986 | European Pat. Off. . |
| 0473551 | 3/1992 | European Pat. Off. . |
| 542685 | 5/1993 | European Pat. Off. . |
| 0542685 | 5/1993 | European Pat. Off. . |
| 9100278 | 1/1991 | WIPO . |
| WO91/00278 | 1/1991 | WIPO . |

OTHER PUBLICATIONS

Ruchardt et al., Chem. Ber. 108:3224–3242 (1975).
Bodanszky et al., Side Reactions in Peptide Synthesis, Synthesis, pp. 333–356 (May, 1981).
Fahrenholtz et al., Journal of Medicinal Chemistry, vol. 17, No. 3, 337–342 (1974).
Miyake et al., Synthetic Communications, 14(4), pp. 353–362 (1984).
Miyake et al., Chemistry, Letters, pp. 123–236 (1985).
Patai, The Chemistry of Carboxylic Acids and Esters, pp. 1–3, Interscience Publishers, London (1969).
Greene et al., Protective Groups in Organic Synthesis, 2nd Ed., p. 1, A. Wiley–Interscience Publications (1991).
Klintz et al, Chemical Abstracts, vol. 119, embry 117271 (1993).
Houben–Weyl, Methoden Der Organischen Chemie, vol. VIII, 1952, pp. 508–513.

*Primary Examiner*—John M. Ford
*Attorney, Agent, or Firm*—Edward McC. Roberts; Marla J. Mathias; William A. Teoli, Jr.

[57] ABSTRACT

3-Aryluracil derivatives of formula I

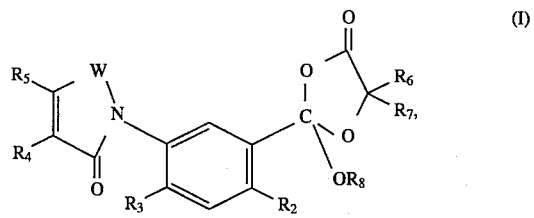

wherein
W is a group of the formula

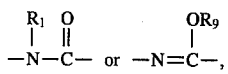

wherein the bond to the ring nitrogen atom is made via the carbon atom; wherein $R_1$ to $R_9$ are as defined in claim 1, are suitable as active ingredients in weed control compositions.

24 Claims, No Drawings

3-ARYLURACIL DERIVATIVES AND THEIR USE AS HERBICIDES

This is a U.S. national stage application filed under 35 USC 371 of international application PCT/EP94/01109, filed Apr. 11, 1994.

The present invention relates to novel, herbicidally active 3-aryluracil derivatives, to processes for their preparation, to compositions comprising those compounds, and to their use in controlling weeds, especially in crops of useful plants, or in inhibiting plant growth.

3-Aryluracils having herbicidal action are known and are described, for example, in WO 91/00278 and EP-A-0 195 346.

Novel 3-aryluracil derivatives having herbicidal and growth-inhibiting properties have now been found.

The present invention accordingly relates to compounds of formula I

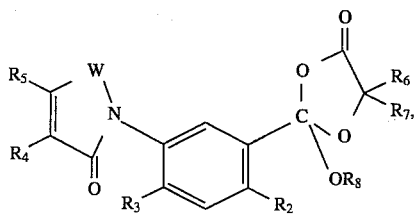

wherein
W is a group of the formula

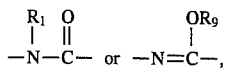

wherein the bond to the ring nitrogen atom is made via the carbon atom;

$R_1$ is hydrogen, $C_1-C_4$alkyl, $C_1-C_4$haloalkyl, $C_3$- or $C_4$-alkenyl or $C_3$- or $C_4$-alkynyl;

$R_2$ is halogen or cyano;

$R_3$ is hydrogen or fluorine;

$R_4$ is hydrogen, halogen or $C_1-C_4$alkyl;

$R_5$ is $C_1-C_4$alkyl or $C_1-C_4$haloalkyl;

$R_6$ and $R_7$ are each independently of the other hydrogen, $C_1-C_8$alkyl, $C_3-C_6$alkenyl, $C_3-C_6$alkynyl, $C_3-C_8$cycloalkyl, $C_1-C_6$haloalkyl, $C_1-C_6$alkoxy-$C_1-C_6$alkyl, $C_1-C_6$-alkylthio-$C_1-C_6$alkyl, aryl, aryl-$C_1-C_4$alkyl, heteroaryl or heteroaryl-$C_1-C_4$alkyl; or $R_6$ and $R_7$ together with the carbon atom to which they are bonded form a 3-, 4-, 5- or 6-membered ring which is unsubstituted or mono- or poly-substituted by $C_1-C_4$alkyl and which may contain —O—, —S— or —N($R_{10}$)— as hetero atom;

$R_8$ is $C_1-C_6$alkyl, cyano-$C_1-C_6$alkyl, nitro-$C_1-C_6$alkyl, $C_3-C_6$alkenyl, $C_3-C_6$alkynyl, $C_1-C_6$haloalkyl, $C_3-C_6$haloalkenyl, $C_3-C_6$cycloalkyl, $C_3-C_6$cycloalkyl-$C_1-C_6$alkyl, aryl, aryl-$C_1-C_4$alkyl, heteroaryl, heteroaryl-$C_1-C_4$alkyl, $C_1-C_6$alkyl-carbonyl-$C_1-C_6$alkyl, $C_1-C_6$alkoxy-$C_1-C_6$alkyl, $C_1-C_6$alkoxy-carbonyl-$C_1-C_6$alkyl, $C_3-C_6$-alkenyloxy-carbonyl-$C_1-C_6$alkyl, $C_1-C_6$alkylthio-$C_1-C_6$alkyl, $C_1-C_6$-dialkylamino-$C_2-C_6$alkyl, oxetanyl or $C_1-C_6$isoalkylideneaminooxy-$C_1-C_4$alkyl;

$R_9$ is $C_1-C_4$alkyl, $C_3$- or $C_4$-alkenyl or $C_3$- or $C_4$-alkynyl; and $R_{10}$ is hydrogen or $C_1-C_4$alkyl;

and, when $R_1$ is hydrogen, the agrochemically acceptable salts of compounds of formula I.

In the formulae I of the 3-aryluracils according to the invention, halogen in the definitions of radicals $R_2$ and $R_4$ is fluorine, chlorine, bromine or iodine, preferably fluorine, chlorine and bromine.

The alkyl, alkenyl and alkynyl radicals $R_1$ and $R_4$ to $R_{10}$ may be straight-chain or branched, and this applies also to the alkyl moiety of haloalkyl, cycloalkylalkyl, alkoxyalkyl, alkoxycarbonylalkyl, alkenyloxycarbonylalkyl, arylalkyl, heteroarylalkyl, alkylthioalkyl, dialkylaminoalkyl, nitro and cyanoalkyl groups. Examples of such alkyl radicals are methyl, ethyl, n-propyl, isopropyl, n-butyl, isobutyl, sec-butyl and tert-butyl, preferably alkyl groups having 1, 2 or 3 carbon atoms; examples of alkenyl radicals that may be mentioned are allyl, 1-methylallyl, methallyl or but-2-en-1-yl, preferably alkenyl radicals having a chain length of 3 or 4 carbon atoms; and examples of alkynyl radicals that may be mentioned are propargyl, but-2-yn-1-yl, 2-methylbutyn-2-yl, but-3-yn-2-yl and pent-4-yn-1-yl, preferably alkynyl radicals having a chain length of 3 or 4 carbon atoms.

The cycloalkyl radical coming into consideration as a substituent in the definitions of $R_6$, $R_7$ and $R_8$ is, for example, cyclopropyl, cyclobutyl, cyclopentyl, cyclohexyl, cycloheptyl or cyclooctyl.

Haloalkyl groups that come into consideration are alkyl groups mono- or poly-substituted, especially mono- to tri-substituted, by halogen (identical or different), the individual meanings of halogen being iodine and especially fluorine, chlorine and bromine, for example trifluoromethyl, 2,2,2-trifluoroethyl or 2-chloro- or 2-bromo-ethyl.

Alkoxyalkyl in the definitions of the radicals $R_6$, $R_7$ and $R_8$ is, for example, methoxymethyl, methoxyethyl, ethoxymethyl, ethoxyethyl, methoxypropyl or ethoxypropyl.

Aryl in the definition of the radicals $R_6$, $R_7$ and $R_8$ is α- or β-naphthyl, especially phenyl; those aromatic rings may contain one or more, identical or different substituents, for example halogen, especially fluorine or chlorine, $C_1-C_3$alkyl, especially methyl, $C_1-C_3$-alkoxy, especially methoxy, trifluoromethyl, nitro and/or cyano.

Heteroaryl in the definition of the radicals $R_6$, $R_7$ and $R_8$ is especially a five- or six-membered aromatic heterocyclic ring, for example 2-, 3- or 4-pyridyl, pyrimidyl, pyrazinyl, furanyl, thienyl, oxazolyl or isoxazolyl, preferably 2- and 3-pyridyl, 2- and 3-furanyl and 2-thienyl.

Alkylthioalkyl in the definitions of the radicals $R_6$, $R_7$ and $R_8$ is, for example, methylthioethyl, ethylthioethyl or methylthiopropyl.

Dialkylaminoalkyl is, for example, N,N-dimethylaminoethyl or N,N-diethylaminoethyl, preferably N,N-dimethylaminoethyl.

Haloalkenyl groups that come into consideration in the definition of the radical $R_8$ are alkenyl groups mono- or poly-substituted by halogen, the individual meanings of halogen being bromine, iodine and especially fluorine and chlorine, for example 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Of the $C_3-C_6$alkenyl radicals that are mono-, di- or tri-substituted by halogen, those radicals having a chain length of 3 or 4 carbon atoms are preferred.

Examples of 3- to 6-membered heterocyclic rings which may be formed by the substituents $R_6$ and $R_7$ together are pyrrolidino, piperidino, N-methylpiperidino, oxetano, thietano, tetrahydrofurano or tetrahydropyrano, preferably oxetano, thietano, tetrahydrofurano and tetrahydropyrano.

The salts of compounds of formula I are especially alkali metal salts, for example sodium and potassium salts; alkaline earth metal salts, for example calcium and magnesium salts; ammonium salts, that is to say unsubstituted ammonium salts and mono- or poly-substituted ammonium salts, and also salts with other organic nitrogen bases.

Accordingly, suitable salt-forming agents are alkali and alkaline earth metal hydroxides, especially the hydroxides of lithium, sodium, potassium, magnesium or calcium, those of sodium or potassium being of particular importance.

Examples of amines suitable for ammonium salt formation include both ammonia and primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, iso-propylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, N-methylmorpholine, thiomorpholine, piperidine, pyrrolidine, indoline, quinuclidine and azepine; primary arylamines, for example anilines, methoxyanilines, ethoxyanilines, o,m,p-toluidines, phenylenediamines, benzidines, naphthylamines and o,m,p-chloroanilines; but especially triethylamine, isopropylamine and diisopropylamine.

The possible presence of at least one asymmetric carbon atom in the compounds of formula I, in the α-position with respect to the carbonyl group in the saturated heterocyclic ring when $R_6$ is different from $R_7$ and/or at the benzyl carbon atom carrying the orthoester group, has the result that the compounds may be either in the form of optically active individual isomers or in the form of racemic mixtures. In the present invention the compounds of formula I are to be understood as being both the pure optical antipodes and the racemates or diastereoisomers. When an aliphatic C=C double bond is present, geometrical isomerism may also occur.

Furthermore, in those compounds of formula I wherein $R_1$ is hydrogen, the possibility of keto-enol tautomerism

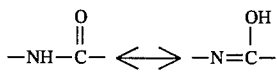

cannot be excluded.

The formula I is intended to cover all those possible isomers and mixtures thereof.

Preference is given to the 3-aryluracil derivatives of formula I wherein $R_2$ is chlorine, bromine or cyano.

Preference is also given to 3-aryluracil derivatives of formula I wherein $R_4$ is hydrogen, fluorine, chlorine, bromine or methyl. Of those compounds, the compounds wherein $R_4$ is hydrogen, fluorine or methyl are especially preferred.

3-Aryluracil derivatives of formula I wherein $R_5$ is methyl, trifluoromethyl or pentafluoroethyl are also preferred.

Preference is likewise given to compounds of formula I wherein $R_6$ and $R_7$ are each independently of the other $C_1$–$C_8$alkyl, $C_3$–$C_6$alkenyl, $C_3$–$C_6$alkynyl, $C_1$–$C_6$haloalkyl, phenyl, furyl, thienyl or pyridyl; or $R_6$ and $R_7$ together with the carbon atom to which they are bonded form a 3-, 4-, 5- or 6-membered unsubstituted ring which may contain —O—, —S— or —N($R_{10}$)— as hetero atom.

Of those compounds of formula I, special preference is given to those wherein $R_6$ and $R_7$ are each independently of the other $C_1$–$C_6$alkyl, $C_3$- or $C_4$-alkenyl, $C_3$- or $C_4$-alkynyl, $C_1$–$C_6$haloalkyl or phenyl; or $R_6$ and $R_7$ together with the carbon atom to which they are bonded form a 3-, 4-, 5- or 6-membered unsubstituted ring which may contain —O— or —S— as hetero atom. Of those compounds special preference is given to the compounds wherein $R_6$ and $R_7$ are each independently of the other $C_1$–$C_6$alkyl or $C_1$–$C_6$haloalkyl; or $R_6$ and $R_7$ together with the carbon atom to which they are bonded form a 3-, 4-, 5- or 6-membered unsubstituted ring.

Importance is also attached to those compounds of formula I wherein $R_8$ is $C_1$–$C_6$alkyl, $C_3$–$C_6$alkenyl, $C_3$–$C_6$alkynyl, $C_1$–$C_6$haloalkyl or $C_1$–$C_6$alkoxy-$C_1$–$C_6$alkyl. Of those compounds of formula I, very special importance is attached to the compounds wherein $R_8$ is $C_1$- or $C_2$-alkyl, $C_3$- or $C_4$-alkenyl, $C_3$- or $C_4$-alkynyl, $C_1$- or $C_2$-haloalkyl or $C_1$- or $C_2$-alkoxy-$C_1$- or -$C_2$-alkyl.

Very special importance is accorded to 3-aryluracil derivatives of formula I wherein the radical W is as defined for formula I; $R_2$ is chlorine, bromine or cyano; $R_3$ is hydrogen or fluorine; $R_4$ is hydrogen, fluorine, chlorine, bromine or methyl; $R_5$ is methyl, trifluoromethyl or pentafluoroethyl; $R_6$ and $R_7$ are each independently of the other $C_1$–$C_8$alkyl, $C_3$- or $C_4$-alkenyl, $C_3$- or $C_4$-alkynyl, $C_1$–$C_3$haloalkyl, phenyl, furyl, thienyl or pyridyl; or $R_6$ and $R_7$ together with the carbon atom to which they are bonded form a 3-, 4-, 5- or 6-membered unsubstituted ring which may contain —O— or —S— as a further hetero atom; and $R_8$ is $C_1$–$C_4$alkyl, $C_3$- or $C_4$-alkenyl, $C_3$- or $C_4$-alkynyl, $C_1$–$C_3$haloalkyl, $C_1$–$C_3$alkoxy-$C_1$–$C_3$alkyl, $C_1$- or $C_2$-alkylthio-$C_2$alkyl, $C_1$- or $C_2$-dialkylamino-$C_2$alkyl, phenyl-$C_1$–$C_3$-alkyl, 2- or 3-pyridyl-$C_1$- or -$C_2$-alkyl, 2- or 3-furyl-$C_1$- or -$C_2$-alkyl or 2-thienyl-$C_1$alkyl.

Especially suitable are 3-aryluracil derivatives of formula I wherein W is a radical of the formula

$R_1$ is hydrogen, $C_1$–$C_4$alkyl, $C_1$–$C_4$haloalkyl, $C_3$- or $C_4$-alkenyl or $C_3$- or $C_4$-alkynyl; $R_5$ is trifluoromethyl; and $R_6$ and $R_7$ are each independently of the other $C_1$–$C_6$alkyl or $C_1$–$C_3$haloalkyl; or $R_6$ and $R_7$ together with the carbon atom to which they are bonded form a 4-, 5- or 6-membered unsubstituted ring.

Also especially suitable are 3-aryluracil derivatives of formula I wherein W is a radical of the formula

$R_9$ is $C_1$–$C_4$alkyl, $C_3$- or $C_4$-alkenyl or $C_3$- or $C_4$-alkynyl; $R_6$ and $R_7$ are each independently of the other $C_1$–$C_6$alkyl or $C_1$–$C_3$haloalkyl; or $R_6$ and $R_7$ together with the carbon atom to which they are bonded form a 4-, 5- or 6-membered unsubstituted ring.

Special importance is also accorded to 3-aryluracil derivatives of formula Ia

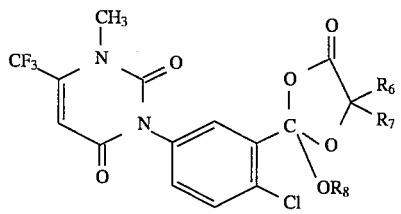

wherein $R_6$ is methyl or ethyl; $R_7$ is $C_1$–$C_8$alkyl, allyl, propargyl, trifluoromethyl, phenyl, 2-furyl, 2-thienyl or 2- or 3-pyridyl; or $R_6$ and $R_7$ together with the carbon atom to which they are bonded form a 3-, 4-, 5- or 6-membered unsubstituted alicyclic ring, an oxetane, tetrahydrofuran, tetrahydropyran or a thietane ring; and $R_8$ is $C_1$–$C_4$alkyl, $C_3$- or $C_4$-alkenyl, $C_3$- or $C_4$-alkynyl, $C_1$alkoxy-$C_2$alkyl, $C_1$alkylthio-$C_2$alkyl, dimethylamino-$C_2$alkyl, 2-bromo- or 2-chloro-$C_2$alkyl, 2,2,2-trifluoro-$C_2$alkyl, phenyl, phenyl-$C_1$- or -$C_2$alkyl, 2- or 3-pyridyl-$C_1$alkyl, 2- or 3-furyl-$C_1$alkyl, 2-thienyl-$C_1$alkyl, 3-oxetanyl or the group —$CH_2CH_2$—O—$N=C(CH_3)_2$. Of those compounds, very special preference is given to the compounds wherein $R_6$ and $R_7$ are each independently of the other methyl or ethyl; and $R_8$ is $C_1$–$C_3$alkyl, allyl, propargyl or phenyl.

Very special importance is attached to compounds of formula Ib

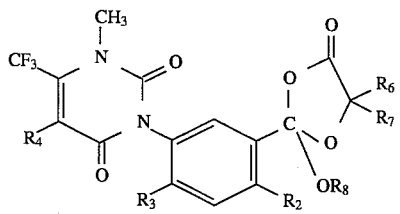

wherein $R_2$ is chlorine, bromine or cyano; $R_3$ is hydrogen or fluorine; $R_4$ is hydrogen, fluorine, chlorine, bromine or methyl; $R_6$ is methyl or ethyl; and $R_7$ and $R_8$ are each independently of the other $C_1$–$C_3$alkyl.

Especially important compounds are also those of formula Ic

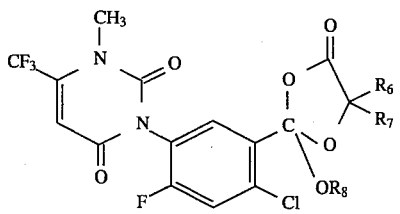

wherein $R_6$ and $R_7$ are each independently of the other methyl or ethyl; and $R_8$ is $C_1$–$C_3$-alkyl, allyl or phenyl.

Especially important compounds are also those of formula Id

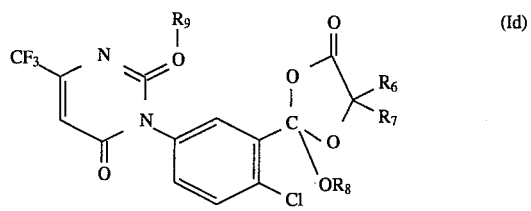

wherein $R_6$ is methyl or ethyl; and $R_7$, $R_8$ and $R_9$ are each independently of the other $C_1$–$C_3$alkyl.

Very special importance is also attached to compounds of formula Ie

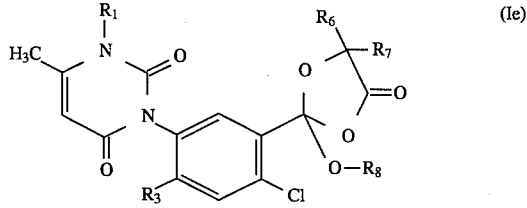

wherein $R_1$ is methyl or difluoromethyl; $R_3$ is hydrogen or fluorine; $R_6$ and $R_7$ are each independently of the other methyl or ethyl; and $R_8$ is $C_3$alkyl.

The process according to the invention for the preparation of the compounds of formula I is carried out analogously to known processes and as follows:
for the preparation of a 3-aryluracil derivative of formula I, a compound of formula II

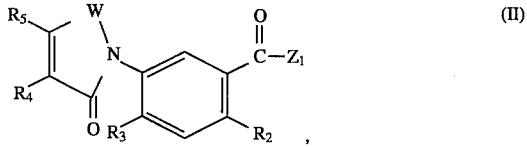

wherein W and $R_2$ to $R_5$ are as defined for formula I and $Z_1$ is a leaving group, for example halogen, preferably fluorine or chlorine, or imidazolide, triazolide or N-hydroxyphthalimide, is reacted with a compound of formula III

wherein $R_6$ and $R_7$ are as defined for formula I and $R_{11}$ is hydrogen or a protecting group, for example allyl, benzyl or p-methoxybenzyl, to form a compound of formula IV

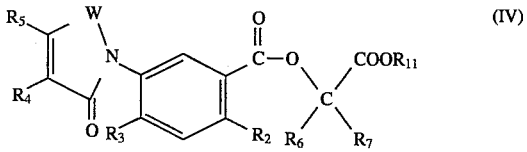

and, when $R_{11}$ is a protecting group, the substituent $R_{11}$ is then removed, and the resulting carboxylic acid of formula V

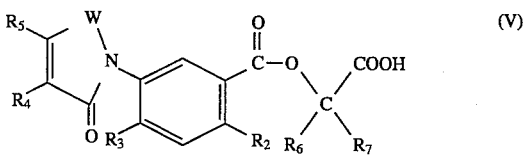

is convened by reaction with a compound of formula VIII $$Q-Z_2 \qquad (VIII),$$

wherein $Z_2$ is a leaving group, especially halogen, and Q is $S(O)Cl-$, $C(O)Cl-$, $PCl_4-$, $C(O)Cl-C(O)-$,

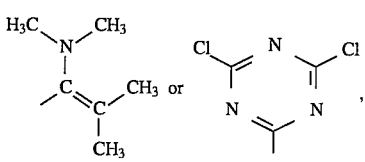

into a compound of formula VI

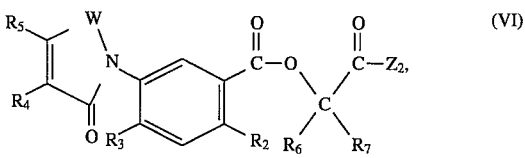

wherein W, $Z_2$ and $R_2$ to $R_7$ are as defined, and finally that compound is reacted under customary conditions with an alcohol of formula VII $$R_8-OH \quad (VII),$$

wherein $R_8$ is as defined for formula I, to form a compound of formula I.

The preparation of the compounds of formula I is in accordance with reaction scheme 1.

Reaction scheme 1:

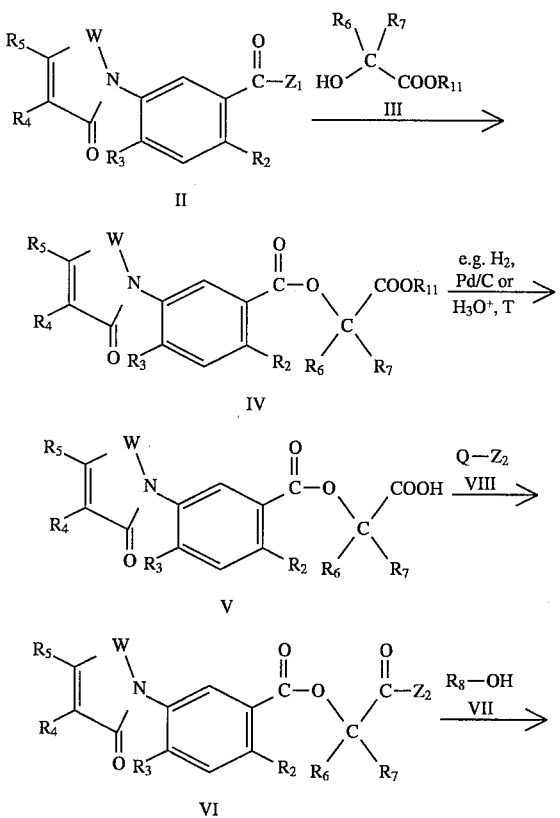

Reaction scheme 1:

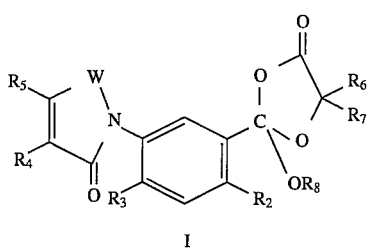

The starting compound of formula II is prepared analogously to known processes, as described, for example, in WO 91/00278.

The esterification of the 3-aryluracil derivative of formula II, wherein $Z_1$ is as defined, with an alcohol of formula III is advantageously carried out analogously to the methods described in S. Patai, "The Chemistry of Carboxylic Acids and Esters", Interscience Publishers, London, 1969; Houben-Weyl, Vol. VIII, page 508 ff.; Synthesis 1981, 333; J. Med. Chem. 17,337 (1974); Synth. Communic. 1984, 353; and Chemistry Lett. 1985, 123.

The removal of the substituent $R_{11}$ in the ester of formula IV when $R_{11}$ is a protecting group can be carried out, for example, by hydrogenolysis or acid catalysis analogously to known methods, as described, for example, in "Protective Groups in Organic Synthesis", Ed. T. W. Green, A. Wiley-Interscience Publications, 1991.

The carboxylic acids of formula V in reaction scheme 1 can also be obtained directly by esterification of a compound of formula II with an α-hydroxycarboxylic acid of formula IIIa

wherein $R_6$ and $R_7$ are as defined for formula I.

The preparation of the activated carboxylic acid derivatives of formula VI wherein $Z_2$ is a leaving group, for example halogen, preferably fluorine or bromine and especially chlorine, is carried out, for example, advantageously by the use of a halogenating agent, for example thionyl halides, for example thionyl chloride or bromide; phosphorus halides or phosphorus oxyhalides, for example phosphorus pentachloride or phosphorus oxychloride or phosphorus pentabromide or phosphoryl bromide; oxalyl halides, for example oxalyl chloride; or phosgene. The reaction is carried out where appropriate in an inert organic solvent, for example n-hexane, benzene, toluene, xylenes, dichloromethane, chloroform, 1,2-dichloroethane or chlorobenzene, at reaction temperatures of from −20° C. to the reflux temperature of the reaction mixture, preferably from 40° to 110° C. in the presence of a catalytic amount of N,N-dimethylformamide. Such reactions are known and a number of variations in respect of the leaving group $Z_2$ are described in the literature.

The cyclisation of a compound of formula VI to form the desired product of formula I can be carried out advantageously in the presence of an alcohol of formula VII in an inert, aprotic, organic solvent, for example chloroform, dichloromethane, 1,2-dichloroethane, cyclohexane, toluene, diethyl ether, tert-butyl methyl ether, ethyl acetate, acetonitrile, N,N-dimethylformamide or dimethyl sulfoxide (DMSO), at reaction temperatures of from −50° C. to the reflux temperature of the reaction mixture in question, preferably from 0° to 20° C., for example as described in Chem. Ber. 108, 3224–3242 (1975).

As an alternative to the data given in the literature, the cyclisation of a compound of formula VI to form the desired product of formula I can also be carried out in the presence of a base, such as sodium hydrogen carbonate, potassium hydrogen carbonate, sodium carbonate, potassium carbonate, calcium carbonate or lithium carbonate, or in the presence of a proton acceptor, such as an epoxyalkyl, for example epoxybutane, epoxycyclohexane or ethylene oxide, or an aluminium silicate, under the same reaction conditions as those described above.

The end products of formula I can be isolated in customary manner by concentration and/or evaporation of the solvent and purified by recrystallisation or trituration of the solid residue in solvents in which they are not readily soluble, such as ethers, alkanes, aromatic hydrocarbons or chlorinated hydrocarbons, or by means of chromatography over a column of silica gel.

The intermediate of formula V is novel. It has been synthesised specifically for the synthesis of the compounds of formula I according to the invention and the present invention relates also thereto.

For the use according to the invention of the compounds of formula I, or compositions comprising them, there come into consideration all the methods of application customary in agriculture, for example pre-emergence application, post-emergence application and seed dressing, and also various methods and techniques, for example the controlled release of active ingredient. For that purpose a solution of the active ingredient is applied to mineral granule carriers or polymerised granules (urea/formaldehyde) and dried. If required, it is also possible to apply a coating (coated granules) which allows the active ingredient to be released in metered amounts over a specific period of time.

The compounds of formula I may be used in unmodified form, that is to say as obtainable from the synthesis, but they are preferably formulated in customary manner together with the adjuvants customarily employed in formulation technology e.g. into emulsifiable concentrates, directly sprayable or dilutable solutions, dilute emulsions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I or at least one compound (active ingredient) of formula I and, where appropriate, one or more solid or liquid adjuvants, are prepared in known manner, e.g. by homogeneously mixing and/or grinding the active ingredients with the adjuvants, e.g. solvents or solid carriers. It is also possible to use surface-active compounds (surfactants) in the preparation of the formulations.

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenol polyethoxyethanols, castor oil poly-glycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology, which may also be used in the compositions according to the invention, are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I-III, Chemical Publishing Co., New York, 1980–1981.

Dr. Helmut Stache "Tensid-Taschenbuch" (Surfactant Handbook), Carl Hanser Verlag, Munich/Vienna 1981.

The herbicidal compositions usually comprise 0.1 to 99%, preferably 0.1 to 95%, of a compound of formula I, 1 to 99% of a solid or liquid formulation adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), antifoams, e.g. silicone oil, preservatives, viscosity regulators, binders and tackifiers, as well as fertilisers or other active ingredients for obtaining special effects.

Preferred formulations have especially the following composition (throughout, percentages are by weight):

| Emulsifiable concentrates | |
|---|---|
| active ingredient | 1 to 90%, preferably 5 to 50% |
| surface-active agent | 5 to 30%, preferably 10 to 20% |
| solvent | 15 to 94%, preferably 70 to 85% |
| Dusts | |
| active ingredient | 0.1 to 50%, preferably 0.1 to 1% |
| solid carrier | 99.9 to 90%, preferably 99.9 to 99% |
| Suspension concentrates | |
| active ingredient | 5 to 75%, preferably 10 to 50% |
| water | 94 to 24%, preferably 88 to 30% |
| surface-active agent | 1 to 40%, preferably 2 to 30% |
| Wettable powders | |
| active ingredient | 0.5 to 90%, preferably 1 to 80% |
| surface-active agent | 0.5 to 20%, preferably 1 to 15% |
| solid carrier | 5 to 95%, preferably 15 to 90% |
| Granules | |
| active ingredient | 0.1 to 30%, preferably 0.1 to 15% |
| solid carrier | 99.5 to 70%, preferably 97 to 85% |

The compounds of formula I are generally used successfully at rates of application of from 0.001 to 2 kg/ha, especially from 0.005 to 1 kg/ha. The concentration required to achieve the desired effect can be determined by experiment. It is dependent upon the type of action, the stage of development of the cultivated plant and of the weed, and also upon the application (place, time, method) and, in dependence on those parameters, can vary within wide limits.

The compounds of formula I are distinguished by growth-inhibiting and herbicidal properties which render them excellently suitable for use in crops of useful plants, especially in cereals, cotton, soybeans, rape, maize, rice and plantations. They can also be used as burn-off agents, for example for potatoes, or as defoliants.

Crops are also to be understood as being those which have been rendered tolerant to herbicides or classes of herbicide by conventional methods of breeding or genetic techniques.

The following Examples further illustrate the invention but do not limit the invention.

Preparation Examples

Example P1: Preparation of carboxy-1-methyl-ethyl-2-chloro-5-[3,6-dihydro-3-methyl-2,6-dioxo-4-trifluoromethyl-1(2H)-pyrimidinyl]-benzoate

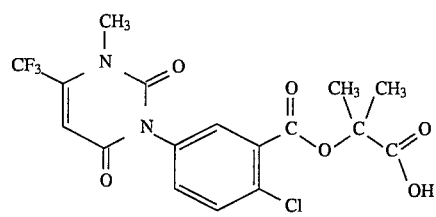

A mixture of 82.0 g of 2-chloro-5-[3,6-dioxo-3-methyl-4-trifluoromethyl-1(2H)-pyrimidinyl]-benzoic acid and 83.3 g of thionyl chloride in 700 ml of toluene is heated at reflux temperature for two hours. The mixture is then concentrated to dryness by evaporation and the residue is dissolved in 600 ml of 1,2-dimethoxyethane. After the dropwise addition of that solution at a temperature of from 10° to 15° C. to a solution of 28.3 g of triethylamine, 0.5 g of 4-dimethylaminopyridine and 29.15 g of α-hydroxyisobutyric acid in 200 ml of 1,2-dimethoxyethane, the reaction mixture is stirred for one hour at 55° C. The reaction mixture is then extracted with 1000 ml of water and three times with 350 ml of ethyl acetate. The organic phase is washed once with 350 ml of water and concentrated by evaporation. The residue is recrystallised from ethyl acetate/n-hexane. The desired product, carboxy-1-methyl-ethyl-2-chloro-5-[3,6-dihydro-3-methyl-2,6-dioxo-4-trifluoromethyl-1(2H)-pyrimidinyl]-benzoate, has a melting point of 202°–203.5° C.

$^1$H-NMR (D$_6$-DMSO, 200 MHz): 13.1 ppm (s, 1H), 7.79 ppm (d,1H), 7.74 ppm (d,1H), 7.53 ppm (d×d,1H), 6.56 ppm (s,1H), 3.40 ppm (s,3H), 1.60 ppm (s,6H).

Carboxy-1-ethyl-propyl-2-chloro-5-[3,6-dihydro-3-methyl-2,6-dioxo-4-trifluoromethyl(2H)-pyrimidinyl]-benzoate, m.p. 162° C., is obtained analogously to Example P1.

Example P2: Preparation of 1-(chlorocarbonyl)-1-methyl-ethyl-2-chloro-5-[3,6-dihydro-3-methyl-2,6-dioxo-4-trifluoromethyl-1(2H)-pyrimidinyl]-benzoate

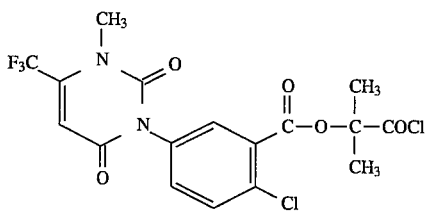

A mixture of 63.0 g of carboxy-1-methyl-ethyl-2-chloro-5-[3,6-dihydro-3-methyl-2,6-dioxo-4-trifluoromethyl- 1(2H)-pyrimidinyl]-benzoate, 43.12 g of thionyl chloride and 0.5 ml of N,N-dimethylformamide in 600 ml of toluene is stirred at reflux temperature for 4 hours. The excess thionyl chloride is then distilled off together with approximately 200 ml of toluene and the residue is then cooled to 0° C. The product crystallises out and is filtered off and then washed twice with 200 ml of petroleum ether each time. The dried product has a melting point of 175° C.

1-(Chlorocarbonyl)-1-ethyl-propyl-2-chloro-5-[3,6-dihydro-3-methyl-2,6-dioxo-4-trifluoromethyl-1(2H)-pyrimidinyl]-benzoate is obtained analogously to Example P2.

Example P3: Preparation of Compound No. 1.001 of Formula

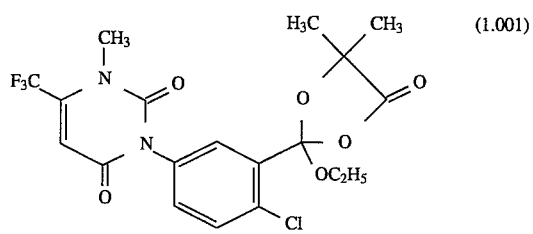

6.8 g of 1-(chlorocarbonyl)-1-methyl-ethyl-2-chloro-5-[3,6-dihydro-3-methyl-2,6-dioxo-4-trifluoromethyl-1(2H)-pyrimidinyl]-benzoate are dissolved in 20 ml of chloroform, and 0.88 g of ethanol is added. At 0°–5° C., a vigorous stream of nitrogen is passed through the reaction solution for 4 hours. The reaction solution is then concentrated by evaporation and the residue is chromatographed over 100 g of silica gel with toluene/ethyl acetate 15:1.20 ml of petroleum ether/toluene 5:1 are added to the residue obtained after concentration of the fractions, and the resulting product is then filtered off and dried; the desired product has a melting point of 55°–57° C.

Example P4: Preparation of Compound No. 1.001 of Formula

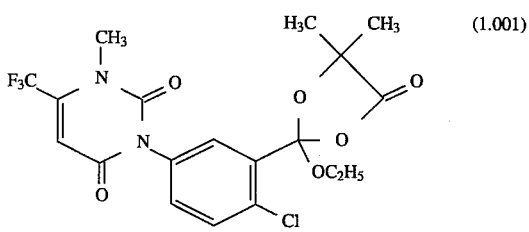

6.8 g of 1-(chlorocarbonyl)-1-methyl-ethyl-2-chloro-5-[3,6-dihydro-3-methyl-2,6-dioxo-4-trifluoromethyl-1(2H)-pyrimidinyl]-benzoate are dissolved in 20 ml of dichloromethane, and 0.88 g of ethanol and 2.5 g of sodium hydrogen carbonate are added at 0° C. The reaction mixture is then stirred for 4 hours at 0° C. and then filtered and the filtrate is concentrated by evaporation. The resulting residue is recrystallised from diethyl ether/petroleum ether. The desired product has a melting point of 55°–57° C.

Analogously to Example P3 or P4 there are obtained compound No. 1.021

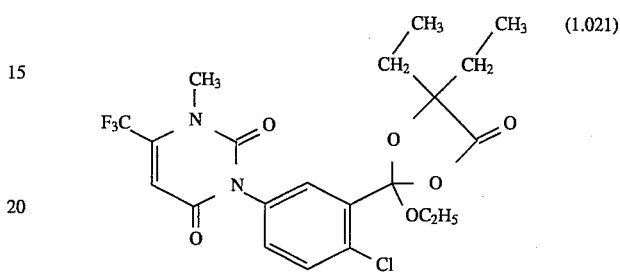

having a melting point of 123°–124° C.; and compound No. 1.022

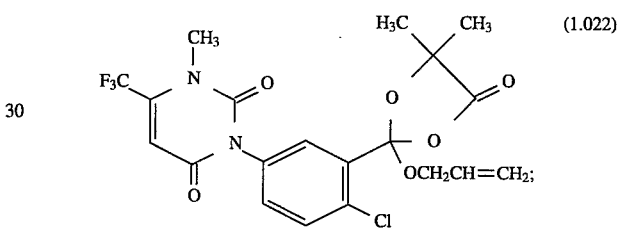

$^1$H-NMR (300 MHz; CDCl$_3$): 7.57 ppm (d, 1H); 7.56 ppm (d, 1H); 7.21 ppm (d×d, 1H); 6.35 ppm (s, 1H); 5.91 ppm (m, 1H); 5.32 ppm (d, 1H); 5.19 ppm (d, 1H); 4.17 ppm (m, 2H); 3.54 ppm (s, 3H); 1.60 ppm (s, 3H); 1.40 ppm (s, 3H).

The compounds listed in Tables 1 to 5 below can be prepared in an analogous manner.

TABLE 1

Compounds of formula Ia

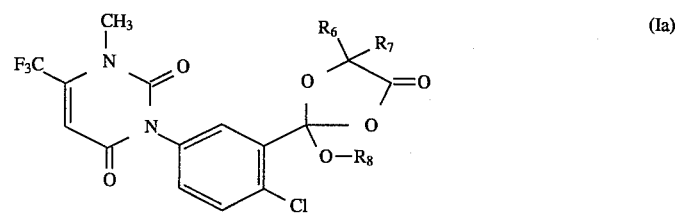

| Comp. No. | R$_6$ | R$_7$ | R$_8$ | Phys. data |
|---|---|---|---|---|
| 1.001 | CH$_3$ | CH$_3$ | C$_2$H$_5$ | m.p. 55–57° C. |
| 1.002 | CH$_3$ | C$_2$H$_5$ | CH$_3$ | m.p. 137–139° C. |
| 1.003 | CH$_3$ | n-C$_3$H$_7$ | CH$_3$ | |
| 1.004 | CH$_3$ | n-C$_3$H$_7$ | CH$_3$ | |
| 1.005 | CH$_3$ | n-C$_4$H$_9$ | CH$_3$ | |

TABLE 1-continued

Compounds of formula Ia

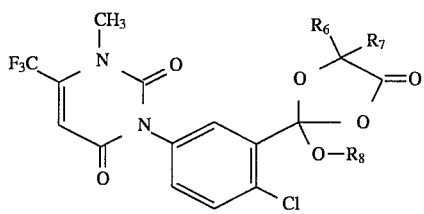

(Ia)

| Comp. No. | $R_6$ | $R_7$ | $R_8$ | Phys. data |
|---|---|---|---|---|
| 1.006 | $CH_3$ | iso$C_4H_9$ | $CH_3$ | |
| 1.007 | $CH_3$ | sec-$C_4H_9$ | $CH_3$ | |
| 1.008 | $CH_3$ | n-$C_5H_{11}$ | $CH_3$ | |
| 1.009 | $CH_3$ | n-$C_6H_{13}$ | $CH_3$ | |
| 1.010 | $CH_3$ | n-$C_7H_{15}$ | $CH_3$ | |
| 1.011 | $CH_3$ | n-$C_8H_{17}$ | $CH_3$ | |
| 1.012 | $CH_3$ | phenyl | $CH_3$ | |
| 1.013 | $CH_3$ | furyl | $CH_3$ | |
| 1.014 | $CH_3$ | thienyl | $CH_3$ | |
| 1.015 | $CH_3$ | 2-pyridyl | $CH_3$ | |
| 1.016 | $CH_3$ | 3-pyridyl | $CH_3$ | |
| 1.017 | $CH_3$ | $-CH_2-CH=CH_2$ | $CH_3$ | |
| 1.018 | $CH_3$ | $-CH_2-C\equiv CH$ | $CH_3$ | |
| 1.019 | $CH_3$ | $CF_3$ | $CH_3$ | |
| 1.020 | $C_2H_5$ | $C_2H_5$ | $CH_3$ | m.p. 148–149° C. |
| 1.021 | $C_2H_5$ | $C_2H_5$ | $C_2H_5$ | m.p. 123–124° C. |
| 1.022 | $CH_3$ | $CH_3$ | $-CH_2-CH=CH_2$ | resin $^1$H-NMR(see above); |
| 1.023 | $C_2H_5$ | $C_2H_5$ | $-CH_2-C\equiv CH$ | |
| 1.024 | $CH_3$ | $CH_3$ | $-CH(CH_3)-C\equiv CH$ | |
| 1.025 | $CH_3$ | $CH_3$ | $-CH(CH_3)-CH=CH_2$ | |
| 1.026 | $CH_3$ | $CH_3$ | $-CH_2-O-CH_3$ | |

TABLE 1-continued

Compounds of formula Ia (Ia)

[Structure: F₃C-C=CH-C(=O)-N(-)-C(=O)-N(CH₃)- where N is connected to a phenyl ring bearing Cl and a C(R₆)(R₇)... group with O-C(=O) and O-R₈ substituents]

| Comp. No. | R₆ | R₇ | R₈ | Phys. data |
|---|---|---|---|---|
| 1.027 | CH₃ | CH₃ | –CH₂–CH₂–O–CH₃ | resin |
| 1.028 | CH₃ | CH₃ | –CH₂–CH₂–O–CH₂–CH₃ | |
| 1.029 | CH₃ | CH₃ | –CH₂–CH₂–S–CH₃ | |
| 1.030 | CH₃ | CH₃ | –CH₂–CH₂–N(CH₃)(CH₃) | |
| 1.031 | CH₃ | CH₃ | –CH₂–CF₃ | |
| 1.032 | CH₃ | CH₃ | –CH₂–CH₂–Cl | |
| 1.033 | CH₃ | CH₃ | –CH₂–CH₂–Br | |
| 1.034 | CH₃ | CH₃ | –CH₂–phenyl | |
| 1.035 | CH₃ | CH₃ | –CH₂–CH₂–phenyl | |
| 1.036 | CH₃ | CH₃ | –CH₂–(2-pyridyl) | |
| 1.037 | CH₃ | CH₃ | –CH(CH₃)–phenyl | |
| 1.038 | CH₃ | CH₃ | –CH₂–(3-pyridyl) | |
| 1.039 | CH₃ | CH₃ | –CH₂–(2-furyl) | |
| 1.040 | CH₃ | CH₃ | –CH₂–(3-furyl) | |
| 1.041 | CH₃ | CH₃ | –CH₂–(2-thienyl) | |

TABLE 1-continued

Compounds of formula Ia

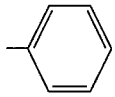

| Comp. No. | R₆ | R₇ | R₈ | Phys. data |
|---|---|---|---|---|
| 1.042 | | —(CH₂)₂— | CH₃ | |
| 1.043 | | —(CH₂)₂— | C₂H₅ | |
| 1.044 | | —(CH₂)₃— | CH₃ | |
| 1.045 | | —(CH₂)₃— | C₂H₅ | |
| 1.046 | | —(CH₂)₄— | CH₃ | |
| 1.047 | | —(CH₂)₄— | C₂H₅ | resin |
| 1.048 | | —(CH₂)₅— | CH₃ | |
| 1.049 | | —(CH₂)₅— | C₂H₅ | |
| 1.050 | | —CH₂—O—CH₂— | CH₃ | |
| 1.051 | | —(CH₂)₃—O— | CH₃ | |
| 1.052 | | —(CH₂)₄—O— | CH₃ | |
| 1.053 | | —CH₂—S—CH₂— | CH₃ | |
| 1.054 | CH₃ | CH₃ | 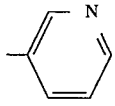 | |
| 1.055 | CH₃ | CH₃ | 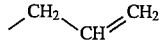 | |
| 1.056 | C₂H₅ | C₂H₅ | —CH₂—CH=CH₂ | m.p. 114–116° C. |
| 1.057 | C₂H₅ | C₂H₅ | C₃H₇(n) | m.p. 94–97° C. |
| 1.058 | C₂H₅ | C₂H₅ | C₃H₇(iso) | m.p. 132–133° C. |
| 1.059 | CH₃ | CH₃ | C₃H₇(n) | resin |
| 1.060 | CH₃ | CH₃ | C₃H₇(iso) | m.p. 71–72° C. |
| 1.061 | CH₃ | CH₃ | —CH₂—C≡CH | resin |
| 1.062 | CH₃ | CH₃ | CH₃ | resin |
| 1.063 | C₂H₅ | C₂H₅ | 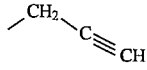 | resin |
| 1.064 | C₂H₅ | C₂H₅ | —CH(CH₃)CH₂CH₃ | |
| 1.065 | | —(CH₂)₃— | C₃H₇(iso) | |
| 1.066 | | —(CH₂)₄— | C₃H₇(iso) | |
| 1.067 | | —(CH₂)₅— | C₃H₇(iso) | |
| 1.068 | | —(CH₂)₂—O—(CH₂)₂— | C₃H₇(iso) | |
| 1.069 | CH₃ | CH₃ | 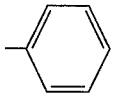 | |
| 1.070 | C₂H₅ | C₂H₅ | 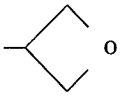 | |
| 1.071 | C₂H₅ | C₂H₅ | —(CH₂)₂O—N=C(CH₃)₂ | |
| 1.072 | C₂H₅ | C₂H₅ | —CH₂COOCH₃ | m.p. 116–118° C. |

TABLE 2

Compounds of formula Ib (Ib) structure with $F_3C$, $N-CH_3$, $R_4$, $R_3$, $R_2$, $R_6$, $R_7$, $R_8$ substituents

| Comp. No. | $R_2$ | $R_3$ | $R_4$ | $R_6$ | $R_7$ | $R_8$ | Phys. data |
|---|---|---|---|---|---|---|---|
| 2.001 | Br | H | H | $CH_3$ | $CH_3$ | $CH_3$ | |
| 2.002 | CN | H | H | $CH_3$ | $CH_3$ | $CH_3$ | |
| 2.003 | CN | F | H | $CH_3$ | $CH_3$ | $CH_3$ | |
| 2.004 | Cl | F | Cl | $CH_3$ | $CH_3$ | $CH_3$ | |
| 2.005 | Cl | F | $CH_3$ | $CH_3$ | $CH_3$ | $CH_3$ | |
| 2.006 | Cl | F | F | $CH_3$ | $CH_3$ | $C_2H_5$ | |
| 2.007 | Br | F | Br | $CH_3$ | $C_2H_5$ | $C_2H_5$ | |
| 2.008 | Br | H | H | $C_2H_5$ | $C_2H_5$ | $C_3H_7$(iso) | |
| 2.009 | Cl | H | H | $C_2H_5$ | $C_2H_5$ | $C_3H_7$(iso) | |
| 2.010 | Cl | H | H | $CH_3$ | $C_2H_5$ | $C_3H_7$(iso) | |

TABLE 3

Compounds of formula Ic (Ic) structure with $F_3C$, $N-CH_3$, F, Cl, $R_6$, $R_7$, $R_8$ substituents

| Comp. No. | $R_6$ | $R_7$ | $R_8$ | Phys. data |
|---|---|---|---|---|
| 3.001 | $CH_3$ | $CH_3$ | $CH_3$ | resin |
| 3.002 | $C_2H_5$ | $CH_3$ | $CH_3$ | |
| 3.003 | $C_2H_5$ | $C_2H_5$ | $C_2H_5$ | |
| 3.004 | $CH_3$ | $CH_3$ | $C_2H_5$ | resin |
| 3.005 | $CH_3$ | $CH_3$ | $-CH_2-CH(-CH_2-)$-phenyl | |
| 3.006 | $C_2H_5$ | $C_2H_5$ | phenyl | resin |
| 3.007 | $C_2H_5$ | $C_2H_5$ | $C_3H_7$(iso) | |
| 3.008 | $CH_3$ | $CH_3$ | $C_3H_7$(iso) | |

TABLE 4

Compounds of formula Id (Id) structure with $F_3C$, $N-R_9$, Cl, $R_6$, $R_7$, $R_8$ substituents

| Comp. No. | $R_6$ | $R_7$ | $R_8$ | $R_9$ | Phys. data |
|---|---|---|---|---|---|
| 4.001 | $CH_3$ | $CH_3$ | $CH_3$ | $CH_3$ | |
| 4.002 | $CH_3$ | $C_2H_5$ | $CH_3$ | $CH_3$ | |
| 4.003 | $CH_3$ | $C_2H_5$ | $C_2H_5$ | $CH_3$ | |
| 4.004 | $CH_3$ | $CH_3$ | $CH_3$ | $C_2H_5$ | |
| 4.005 | $C_2H_5$ | $C_2H_5$ | $C_3H_7$(iso) | $CH_3$ | |
| 4.006 | $CH_3$ | $CH_3$ | $C_3H_7$(iso) | $CH_3$ | |

TABLE 5

Compounds of formula Ie (Ie) structure with $H_3C$, $N-R_1$, $R_3$, Cl, $R_6$, $R_7$, $R_8$ substituents

| Comp. No. | $R_1$ | $R_3$ | $R_6$ | $R_7$ | $R_8$ | Phys. data |
|---|---|---|---|---|---|---|
| 5.001 | $CH_3$ | H | $C_2H_5$ | $C_2H_5$ | $C_3H_7$(iso) | |
| 5.002 | $CH_3$ | F | $C_2H_5$ | $C_2H_5$ | $C_3H_7$(iso) | |
| 5.003 | $CH_3$ | H | $CH_3$ | $CH_3$ | $C_3H_7$(iso) | |
| 5.004 | $CHF_2$ | H | $CH_3$ | $CH_3$ | $C_3H_7$(iso) | |
| 5.005 | $CHF_2$ | F | $CH_3$ | $CH_3$ | $C_3H_7$(iso) | |

Formulation Examples for Active Ingredients of Formula I
(Throughout, Percentages are by Weight)

| F1. Emulsifiable concentrates | a) | b) | c) | d) |
|---|---|---|---|---|
| a compound of Tables 1–5 | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| a compound of Tables 1–5 | 5% | 10% | 50% | 90% |
| dipropylene glycol methyl ether | — | 20% | 20% | — |
| polyethylene glycol (mol.wt.400) | 20% | 10% | — | — |
| N-methyl-2-pyrrolidone | — | — | 30% | 10% |
| aromatic hydrocarbon mixture $C_9$–$C_{12}$ | 75% | 60% | — | — |

The solutions are suitable for application in the form of micro-drops.

| F3. Wettable powders | a) | b) | c) | d) |
|---|---|---|---|---|
| a compound of Tables 1–5 | 5% | 25% | 50% | 80% |
| sodium lignosulfonate | 4% | — | 3% | — |
| sodium laurylsulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, affording wettable powders which can be diluted with water to give suspensions of any desired concentration.

| F4. Coated granules | a) | b) | c) |
|---|---|---|---|
| a compound of Tables 1–5 | 0.1% | 5% | 15% |
| highly dispersed silicic acid | 0.9% | 2% | 2% |
| inorganic carrier (diameter 0.1–1 mm) e.g. CaCO$_3$ or SiO$_2$ | 99.0% | 93% | 83% |

The active ingredient is dissolved in methylene chloride, the solution is sprayed onto the carrier, and the solvent is subsequently evaporated off in vacuo.

| F5. Coated granules | a) | b) | c) |
|---|---|---|---|
| a compound of Tables 1–5 | 0.1% | 5% | 15% |
| polyethylene glycol (mol.wt. 200) | 1.0% | 2% | 3% |
| highly dispersed silicic acid | 0.9% | 1% | 2% |
| inorganic carrier (diameter 0.1–1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| a compound of Tables 1–5 | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The mixture is extruded and then dried in a stream of air.

| F7. Dusts | a) | b) | c) |
|---|---|---|---|
| a compound of Tables 1–5 | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| a compound of Tables 1–5 | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

Biological Examples

Example B1: Pre-Emergence Herbicidal Action

Monocotyledonous and dicotyledonous test plants are sown in standard soil in plastic pots. Immediately after sowing, an aqueous suspension of the test compounds prepared from a 25% wettable powder formulation (Example F3, b)) is applied by spraying at a rate of application corresponding to 2 kg of active ingredient/hectare (500 l water/ha). The test plants are then cultivated in a greenhouse under optimum conditions. After 3 weeks the test is evaluated in accordance with a scale of nine ratings (1=total damage, 9=no action). Ratings of from 1 to 4 (especially from 1 to 3) indicate good to very good herbicidal action.

TABLE B1

| | Pre-emergence action | | | |
|---|---|---|---|---|
| | Test plant | | | |
| Compound No. | Avena | Setaria | Sinapis | Stellaria |
| 1.001 | 1 | 1 | 1 | 1 |
| 1.021 | 1 | 1 | 1 | 1 |
| 1.022 | 1 | 1 | 1 | 1 |

The same results are obtained when compounds of formula I are formulated in accordance with Examples F1, F2 and F4 to F8.

Example B2: Post-Emergence Herbicidal Action (Contact Herbicide)

In a greenhouse, monocotyledonous and dicotyledonous test plants are raised in plastic pots containing standard soil and at the 4- to 6-leaf stage are sprayed with an aqueous suspension of the test compounds of formula I prepared from a 25% wettable powder formulation (Example F3, b)) at a rate of application corresponding to 2000 g of active ingredient/ha (500 l water/ha). The test plants are then grown on in the greenhouse under optimum conditions. After about 18 days the test is evaluated in accordance with a scale of nine ratings (1=total damage, 9=no action). Ratings of from 1 to 4 (especially from 1 to 3) indicate good to very good herbicidal action.

TABLE B2

| | Post-emergence action | | | |
|---|---|---|---|---|
| | Test plant | | | |
| Compound No. | Avena | Setaria | Sinapis | Stellaria |
| 1.001 | 1 | 1 | 1 | 1 |
| 1.021 | 1 | 1 | 1 | 1 |
| 1.022 | 1 | 1 | 1 | 1 |

The same results are obtained when compounds of formula I are formulated in accordance with Examples F1, F2 and F4 to F8.

What is claimed is:

1. A compound of formula I

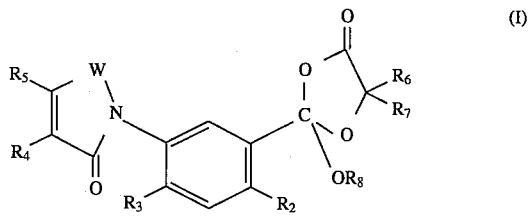

wherein

W is a group of the formula

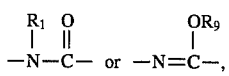

wherein the bond to the ring nitrogen atom is made via the carbon atom;

$R_1$ is hydrogen, $C_1$–$C_4$alkyl, $C_1$–$C_4$haloalkyl, $C_3$- or $C_4$-alkenyl or $C_3$- or $C_4$-alkynyl;

$R_2$ is halogen or cyano;

$R_3$ is hydrogen or fluorine;

$R_4$ is hydrogen, halogen or $C_1$–$C_4$alkyl;

$R_5$ is $C_1$–$C_4$alkyl or $C_1$–$C_4$haloalkyl;

$R_6$ and $R_7$ are each independently of the other hydrogen, $C_1$–$C_8$alkyl, $C_3$–$C_6$alkenyl, $C_3$–$C_6$alkynyl, $C_3$–$C_8$cycloalkyl, $C_1$–$C_6$haloalkyl, $C_1$–$C_6$alkoxy-$C_1$–$C_6$alkyl, $C_1$–$C_6$alkylthio-$C_1$–$C_6$alkyl, α- or β-naphthyl, phenyl, α- or β-naphthyl-$C_1$–$C_4$alkyl, phenyl-$C_1$–$C_4$alkyl, 2-, 3- or 4-pyridyl, pyrimidyl, pyrazinyl, furanyl, thienyl, oxazolyl, isoxazolyl or 2-, 3- or 4-pyridyl-$C_1$–$C_4$alkyl, pyrimidyl-$C_1$–$C_4$alkyl, pyrazinyl-$C_1$–$C_4$alkyl, furanyl-$C_1$–$C_4$alkyl, thienyl-$C_1$–$C_4$alkyl, oxazolyl-$C_1$–$C_4$alkyl, isoxazolyl-$C_1$–$C_4$alkyl; or $R_6$ and $R_7$ together with the carbon atom to which they are bonded form a 3-, 4-, 5- or 6-membered ring which is unsubstituted or mono- or poly-substituted by $C_1$–$C_4$alkyl and which in addition may have one —O—, —S— or —N($R_{10}$)— as hetero atom, at the 2-, 3- or 4-position, the 1-position being the carbon atom of the cyclic ortho-ester moiety to which the ring forming substituents $R_6$ and $R_7$ are bonded;

$R_8$ is $C_1$–$C_6$alkyl, cyano-$C_1$–$C_6$alkyl, nitro-$C_1$–$C_6$alkyl, $C_3$–$C_6$alkenyl, $C_3$–$C_6$alkynyl, $C_1$–$C_6$-haloalkyl, $C_3$–$C_6$-haloalkenyl, $C_3$–$C_6$cycloalkyl, $C_3$–$C_6$cycloalkyl-$C_1$–$C_6$alkyl, α- or β-naphthyl, phenyl, α- or β-naphthyl-$C_1$–$C_4$alkyl, phenyl-$C_1$–$C_4$alkyl, 2-, 3- or 4-pyridyl, pyrimidyl, pyrazinyl, furanyl, thienyl, oxazolyl, isoxazolyl, 2-, 3- or 4-pyridyl-$C_1$–$C_4$alkyl, pyrimidyl-$C_1$–$C_4$alkyl, pyrazinyl-$C_1$–$C_4$alkyl, furanyl-$C_1$–$C_4$alkyl, thienyl-$C_1$–$C_4$alkyl, oxazolyl-$C_1$–$C_4$alkyl, isoxazolyl-$C_1$–$C_4$alkyl, $C_1$–$C_6$alkyl-carbonyl-$C_1$–$C_6$alkyl, $C_1$–$C_6$alkoxy-$C_1$–$C_6$alkyl, $C_1$–$C_6$alkoxy-carbonyl-$C_1$–$C_6$alkyl, $C_3$–$C_6$alkenyloxy-carbonyl-$C_1$–$C_6$alkyl, $C_1$–$C_6$alkylthio-$C_1$–$C_6$alkyl, $C_1$–$C_6$-dialkylamino-$C_2$–$C_6$alkyl, oxetanyl or $C_1$–$C_6$isoalkylideneaminooxy-$C_1$–$C_4$alkyl;

$R_9$ is $C_1$–$C_4$alkyl, $C_3$- or $C_4$-alkenyl or $C_3$- or $C_4$-alkynyl; and $R_{10}$ is hydrogen or $C_1$–$C_4$alkyl; or, when $R_1$ is hydrogen, an agrochemically acceptable salt of a compound of formula I.

2. A compound according to claim 1 wherein $R_2$ is chlorine, bromine or cyano.

3. A compound according to claim 1 wherein $R_4$ is hydrogen, fluorine, chlorine, bromine or methyl.

4. A compound according to claim 3 wherein $R_4$ is hydrogen, fluorine or methyl.

5. A compound according to claim 1 wherein $R_5$ is methyl, trifluoromethyl or pentafluoroethyl.

6. A compound according to claim 1 wherein $R_6$ and $R_7$ are each independently of the other $C_1$–$C_8$alkyl, $C_3$–$C_6$alkenyl, $C_3$–$C_6$alkynyl, $C_1$–$C_6$haloalkyl, phenyl, furyl, thienyl or pyridyl: or $R_6$ and $R_7$ together with the carbon atom to which they are bonded form a 3-, 4-, 5- or 6-membered unsubstituted ring which may have one —O—, —S— or —N($R_{10}$)— as hetero atom, at the 2-, 3- or 4-position, the 1-position being the carbon atom of the cyclic ortho-ester moiety to which the ring forming substituents $R_6$ and $R_7$ are bonded.

7. A compound according to claim 6 wherein $R_6$ and $R_7$ are each independently of the other $C_1$–$C_6$alkyl, $C_3$- or $C_4$-alkenyl, $C_3$- or $C_4$-alkynyl, $C_1$–$C_6$haloalkyl or phenyl; or $R_6$ and $R_7$ together with the carbon atom to which they are bonded form a 3-, 4-, 5- or 6-membered unsubstituted ring which may have one —O— or —S— as hetero atom, at the 2-, 3- or 4-position, the 1-position being the carbon atom of the cyclic ortho-ester moiety to which the ring forming substituents $R_6$ and $R_7$ are bonded.

8. A compound according to claim 7 wherein $R_6$ and $R_7$ are each independently of the other $C_1$–$C_6$alkyl or $C_1$–$C_6$haloalkyl; or $R_6$ and $R_7$ together with the carbon atom to which they are bonded form a 3-, 4-, 5- or 6-membered unsubstituted ring.

9. A compound according to claim 1 wherein $R_8$ is $C_1$–$C_6$alkyl, $C_3$–$C_6$alkenyl, $C_3$–$C_6$-alkynyl, $C_1$–$C_6$haloalkyl or $C_1$–$C_6$alkoxy-$C_1$–$C_6$alkyl.

10. A compound according to claim 9 wherein $R_8$ is $C_1$- or $C_2$-alkyl, $C_3$- or $C_4$-alkenyl, $C_3$- or $C_4$-alkynyl, $C_1$- or $C_2$-haloalkyl or $C_1$- or $C_2$-alkoxy-$C_1$- or -$C_2$-alkyl.

11. A compound according to claim 1 wherein the radical W is as defined in claim 1; $R_2$ is chlorine, bromine or cyano; $R_3$ is hydrogen or fluorine; $R_4$ is hydrogen, fluorine, chlorine, bromine or methyl; $R_5$ is methyl, trifluoromethyl or pentafluoroethyl; $R_6$ and $R_7$ are each independently of the other $C_1$–$C_8$alkyl, $C_3$- or $C_4$-alkenyl, $C_3$- or $C_4$-alkynyl, $C_1$–$C_3$haloalkyl, phenyl, furyl, thienyl or pyridyl; or $R_6$ and $R_7$ together with the carbon atom to which they are bonded form a 3-, 4-, 5- or 6-membered unsubstituted ring which may have one —O— or —S— as hetero atom, at the 2-, 3- or 4-position, the 1-position being the carbon atom of the cyclic ortho-ester moiety to which the ring forming substituents $R_6$ and $R_7$ are bonded; and $R_8$ is $C_1$–$C_4$alkyl, $C_3$- or $C_4$-alkenyl, $C_3$- or $C_4$-alkynyl, $C_1$–$C_3$haloalkyl, $C_1$–$C_3$alkoxy-$C_1$–$C_3$alkyl, $C_1$- or $C_2$-alkylthio-$C_2$alkyl, $C_1$- or $C_2$-dialkylamino-$C_2$alkyl, phenyl-$C_1$–$C_3$alkyl, 2- or 3-pyridyl-$C_1$- or -$C_2$-alkyl, 2- or 3-furyl-$C_1$- or -$C_2$-alkyl or 2-thienyl-$C_1$alkyl.

12. A compound according to claim 11 wherein W is a radical of the formula $$\begin{array}{c} R_1 \quad O \\ | \quad \| \\ -N-C- \end{array};$$

$R_1$ is hydrogen, $C_1$–$C_4$alkyl, $C_1$–$C_4$haloalkyl, $C_3$- or $C_4$-alkenyl or $C_3$- or $C_4$-alkynyl; $R_5$ is trifluoromethyl; and $R_6$ and $R_7$ are each independently of the other $C_1$–$C_6$alkyl or $C_1$–$C_3$haloalkyl; or $R_6$ and $R_7$ together with the carbon atom to which they are bonded form a 4-, 5- or 6-membered unsubstituted ring.

13. A compound according to claim 11 wherein W is a radical of the formula $$\begin{array}{c} OR_9 \\ | \\ -N=C- \end{array};$$

$R_9$ is $C_1$–$C_4$alkyl, $C_3$- or $C_4$-alkenyl or $C_3$- or $C_4$-alkynyl; $R_6$ and $R_7$ are each independently of the other $C_1$–$C_6$alkyl or $C_1$–$C_3$haloalkyl; or $R_6$ and $R_7$ together with the carbon atom to which they are bonded form a 4-, 5- or 6-membered unsubstituted ring.

14. A compound according to claim 11 of formula Ia (Ia)

[structure]

wherein $R_6$ is methyl or ethyl; $R_7$ is $C_1$–$C_8$alkyl, allyl, propargyl, trifluoromethyl, phenyl, 2-furyl, 2-thienyl or 2- or 3-pyridyl; or $R_6$ and $R_7$ together with the carbon atom to which they are bonded form a 3-, 4-, 5- or 6-membered unsubstituted alicyclic ring, an oxetane, tetrahydrofuran, tetrahydropyran or a thietane ring; and $R_8$ is $C_1$–$C_4$alkyl, $C_3$- or $C_4$-alkenyl, $C_3$- or $C_4$-alkynyl, $C_1$alkoxy-$C_2$alkyl, $C_1$alkylthio-$C_2$alkyl, dimethylamino-$C_2$-alkyl, 2-bromo- or 2-chloro-$C_2$alkyl, 2,2,2-trifluoro-$C_2$alkyl, phenyl, phenyl-$C_1$- or -$C_2$-alkyl, 2- or 3-pyridyl-$C_1$alkyl, 2- or 3-furyl-$C_1$alkyl, 2-thienyl-$C_1$alkyl, 3-oxetanyl or the group —$CH_2CH_2$—O—N=$C(CH_3)_2$.

15. A compound according to claim 14 wherein $R_6$ and $R_7$ are each independently of the other methyl or ethyl; and $R_8$ is $C_1$–$C_3$alkyl, allyl, propargyl or phenyl.

16. A compound according to claim 11 of formula Ib (Ib)

[structure]

wherein $R_2$ is chlorine, bromine or cyano; $R_3$ is hydrogen or fluorine; $R_4$ is hydrogen, fluorine, chlorine, bromine or methyl; $R_6$ is methyl or ethyl; and $R_7$ and $R_8$ are each independently of the other $C_1$–$C_3$alkyl.

17. A compound according to claim 11 of formula Ic (Ic)

[structure]

wherein $R_6$ and $R_7$ are each independently of the other methyl or ethyl; and $R_8$ is $C_1$–$C_3$-alkyl, allyl or phenyl.

18. A compound according to claim 11 of formula Id (Id)

[structure]

wherein $R_6$ is methyl or ethyl; and $R_7$, $R_8$ and $R_9$ are each independently of the other $C_1$–$C_3$alkyl.

19. A compound according to claim 11 of formula Ie (Ie)

[structure]

wherein $R_1$ is methyl or difluoromethyl; $R_3$ is hydrogen or fluorine; $R_6$ and $R_7$ are each independently of the other methyl or ethyl; and $R_8$ is $C_3$alkyl.

20. A compound of formula V (V)

[structure]

wherein the group W and $R_2$ to $R_5$ are as defined in claim 1; $R_6$ and $R_7$ are each independently of the other $C_3$–$C_6$alkenyl, $C_3$–$C_6$alkynyl, $C_3$–$C_8$cycloalkyl, $C_1$–$C_6$haloalkyl, $C_1$–$C_6$alkoxy-$C_1$–$C_6$alkyl, $C_1$–$C_6$alkylthio-$C_1$–$C_6$alkyl, α- or β-naphthyl, phenyl, α- or β-naphthyl-$C_1$–$C_4$alkyl, phenyl-$C_1$–$C_4$alkyl, 2-, 3- or 4-pyridyl, pyrimidyl, pyrazinyl, furanyl, thienyl, oxazolyl, isoxazolyl or 2-, 3- or 4-pyridyl-$C_1$–$C_4$alkyl, pyrimidyl-$C_1$–$C_4$alkyl, pyrazinyl-$C_1$–$C_4$alkyl, furanyl-$C_1$–$C_4$alkyl, thienyl-$C_1$–$C_4$alkyl, oxazolyl-$C_1$–$C_4$alkyl, isoxazolyl-$C_1$–$C_4$alkyl; or $R_6$ and $R_7$ together with the carbon atom to which they are bonded form a 3-, 4-, 5- or 6-membered ring which is unsubstituted or mono- or poly-substituted by $C_1$–$C_4$alkyl and which in addition may have one —O—, —S— or —N($R_{10}$)— as hetero atom, at the 2-, 3- or 4-position, the 1-position being the carbon atom of the cyclic ortho-ester moiety to which the ring forming substituents $R_6$ and $R_7$ are bonded; and $R_{10}$ is hydrogen or $C_1$–$C_4$alkyl.

21. A herbicidal and plant growth-inhibiting composition comprising one or more compounds of formula I according to claim 1 and an inert carrier.

22. A composition according to claim 21, comprising from 0.1 to 95% by weight of a compound of formula I.

23. A method of controlling undesired plant growth which comprises treating the crop plants to be protected against weeds or treating the weeds or treating the crop plants and the weeds with a compound of formula I according to claim 1 or with a composition comprising such a compound and an inert carrier.

24. A method according to claim 23, which comprises the application of a compound of formula I in an amount of from 0.001 to 2 kg per hectare.

* * * * *